United States Patent
Choi et al.

(10) Patent No.: US 7,202,043 B2
(45) Date of Patent: Apr. 10, 2007

(54) DETECTING CELL MEMBRANE PROTEIN ENDOCYTOSIS

(75) Inventors: Yun-Jung Choi, Fremont, CA (US); Kun Peng, San Jose, CA (US); Linda Kauffman, San Carlos, CA (US); Rajendra Singh, San Jose, CA (US)

(73) Assignee: Discover Corporation, Fremont, CA (US)

( * ) Notice: Subject to any disclaimer, the term of this patent is extended or adjusted under 35 U.S.C. 154(b) by 0 days.

(21) Appl. No.: 11/244,256

(22) Filed: Oct. 4, 2005

(65) Prior Publication Data

US 2006/0073523 A1     Apr. 6, 2006

Related U.S. Application Data

(60) Provisional application No. 60/615,851, filed on Oct. 4, 2004.

(51) Int. Cl.
*G01N 33/53* (2006.01)
(52) U.S. Cl. .................. 435/7.2; 435/7.21; 435/7.6; 435/962; 435/963
(58) Field of Classification Search ............... 435/7.2, 435/7.21, 7.6, 962, 963
See application file for complete search history.

(56) References Cited

U.S. PATENT DOCUMENTS

| | | | |
|---|---|---|---|
| 6,759,206 B1 * | 7/2004 | Rubin et al. | 435/7.2 |
| 2005/0136488 A1 * | 6/2005 | Horecka et al. | 435/7.2 |
| 2006/0246507 A1 * | 11/2006 | Heding | 435/7.1 |

* cited by examiner

*Primary Examiner*—David A. Saunders
(74) *Attorney, Agent, or Firm*—David J. Aston; Peters Verny, LLP; Bertram Rowland (57) ABSTRACT

Methods and reagents are provided for determining endocytosis, using a cell expressing an externally polypeptide labeled cell membrane receptor, and as a reagent an antibody to said label conjugated to a fragment of an enzyme fragment complementation pair. Compounds are tested for their effect on endocytosis by complexing the reagent with said cells, adding the test compound at any time in relation to the complexing, allowing any endocytosis to occur, proteolytically degrading external enzyme fragment, adding protease inhibitor and the complementary member of the enzyme fragment complementation pair and substrate. The product provides a detectable signal related to the amount of endocytosis that occurred. The method is readily automated as all steps can occur in a single vessel without separations and washings.

10 Claims, 1 Drawing Sheet

Figure 1

SEQUENCE LISTING

```
<160> NUMBER OF SEQ ID NOS: 2

<210> SEQ ID NO 1
<211> LENGTH: 8
<212> TYPE: PRT
<213> ORGANISM: artificial sequence
<220> FEATURE:
<223> OTHER INFORMATION: FLAG epitope

<400> SEQUENCE: 1

Asp Tyr Lys Asp Asp Asp Asp Lys
1               5

<210> SEQ ID NO 2
<211> LENGTH: 23
<212> TYPE: PRT
<213> ORGANISM: artificial sequence
<220> FEATURE:
<223> OTHER INFORMATION: FLAG epitope

<400> SEQUENCE: 2

Met Asp Tyr Lys Asp His Asp Gly Asp Tyr Lys Asp His Asp Ile Asp
1               5                   10                  15

Tyr Lys Asp Asp Asp Asp Lys
            20
```

DETECTING CELL MEMBRANE PROTEIN ENDOCYTOSIS

CROSS-REFERENCE TO RELATED APPLICATIONS

This application claims priority from U.S. Provisional Patent Application No. 60/615,851 filed on Oct. 4, 2004, which is hereby incorporated by reference in its entirety.

REFERENCE TO SEQUENCE LISTING

None

BACKGROUND OF THE INVENTION

1. Field of the Invention

The field of this invention is high throughput screening assays for endocytosis.

2. Background

The ability to identify proteins involved in cellular pathways, map out the pathways and the proteins involved at the various stages and relate these to a phenotype has greatly expanded the need to identify the effect of various agents on the cellular phenotype and the target(s) for causing the effect. The interest in being able to identify compounds that are able to modulate the activity of a target and the increasing ability to prepare compounds has necessitated the development of protocols that allow for rapid and accurate evaluation of the activity of compounds, not only against the individual target. In order to have a successful assay, a significant number of requirements should be met. While ideally all of the requirements should be met, there will usually be compromises as to each of the requirements to provide a protocol that fulfills the overall needs of the user.

An efficient protocol will be accurate, repeatable, rapid, use conventional equipment, require as few steps as possible, particularly avoiding procedures that can introduce errors such as separations and washings, require readily available reagents, be adaptable for a number of determinations with different targets, require small volumes of sample and reagents, conveniently be performed in microtiter well plates, be robust and provide comparable results when performed in different venues. Fluorescent assays have many of these capabilities, but in many cases do not have the desired sensitivity, particularly where there is only one fluorescent molecule for each event. In some instances, it is desirable to have fusion proteins that can act as surrogates for the target proteins. The advent of green fluorescent protein and other fluorescent proteins has provided the opportunity to fuse the fluorescent protein with the target protein, but the quantum efficiency of these proteins is relatively low. Therefore, frequently to detect trafficking of the protein, it is expressed at high levels. These high levels can be deleterious to the cell, changing its phenotype and even leading to mortality.

Enzymes are attractive as labels, since they provide for amplification of signal by using a substrate whose product can be detected. Protocols can be devised that allow for a homogeneous assay without requiring separation and washing steps that introduce error into the results.

An important aspect of cellular activity is the protein population on the cell surface. Cellular membrane proteins fulfill many functions in transducing signals when ligand binds, acting as ion channels, binding to other proteins involving diapedesis, viral nucleic acid insertion, immune synapse, etc. For many receptors of clinical interest, upon binding to ligand, the cellular membrane receptor becomes endocytosed, so that the population at the surface may change in the presence of ligand or an agonist. When studying candidate compounds that may find use as drugs, acting as agonists or antagonists, one is interested in the amount of the cellular membrane protein that is endocytosed. By measuring the amount of protein that is endocytosed, one can measure the amount of binding of ligand or a mimetic ligand to the receptor, providing for a measure of the activity of the ligand or its mimetic analog.

Relevant Literature

Literature references of interest include Tsao and von Zastrow, 2000, J of Biol Chem 275, 11130–40; Neve, et al., 2001 Biochem Biophys Res Comm 280, 274–9; Liang and Huganir 2001 J of Neurochemistry 77, 1626–31; and Adie, et al., 2003 Assay and Drug Development Technologies 1, 251–9. Patent references of interest include US2002/0182643; US2004/0024005; US2004/0101912; and WO 02/033044.

BRIEF SUMMARY OF THE INVENTION

Protocols and reagents are provided for determining surface membrane proteins that are endocytosed using a membrane fusion protein having an external member of a specific binding pair bound to the surface membrane protein and a reagent comprising the complementary member of the specific binding pair bound to an enzyme complementation fragment ("EFC") of an enzyme complementation fragment pair (an enzyme donor ("ED") and and enzyme acceptor ("EA"). The fusion protein serves as a surrogate for the target surface membrane protein. The reagent is added to the cells and binds to its complementary member bound to the cell membrane. After providing conditions for determining whether endocytosis occurs, the activity of the reagent is inhibited. The cells are then lysed and the complementary member of the enzyme complementation pair added to form an active enzyme as well as substrate and the amount of product produced measured. Depending on the nature of the inhibition, additional reagents may be added to prevent inhibition of the endocytosed reagent. The amount of product is a measure of the amount of the surface membrane fusion protein that was endocytosed. The protocol uses a single vessel without separation or washing steps that can introduce large errors. In this way candidate compounds can be investigated as to their ability to cause endocytosis of a target surface membrane protein.

DETAILED DESCRIPTION OF THE PREFERRED EMBODIMENT

Methods and compositions are provided for determining the amount of endocytosis of a surface membrane protein. The compositions employed include a cell having a nucleic acid expression construct expressing a surface membrane protein fused to an external member of a specific binding pair. Also included is a reagent comprising a complementary member of the specific binding pair joined to a member of an enzyme fragment complementation pair, which when complexed to its complementary member forms an active enzyme. In addition there are enzyme substrate and ancillary components used at the various stages.

The method employs cells expressing the surface membrane protein fused to an external member of a specific binding pair. To the cells in an appropriate medium is added the reagent and the medium incubated for sufficient time for the reagent to bind to the complementary member of the specific binding pair. If desired, the complex of cells and reagent may be prepared earlier for use in the assay. The environment is then modified, usually by adding a candidate compound to be tested for its ability to induce or inhibit endocytosis, depending upon whether the compound is an agonist or antagonist. The modification of the environment may occur at any time in relation to the complexing of the reagent and cells, prior, simultaneously, or subsequently, but is preferably added subsequently. After incubation for sufficient time for endocytosis to occur, the reagent is inhibited. After lysing the cells, the reagent which was endocytosed is measured by adding the complementary member of the enzyme fragment complementation pair and substrate and the enzyme product measured as a measure of the amount of reagent present. The determination may be a point determination at a specific time, a multiplicity of points or a rate determination, where the addition of the last component necessary for the enzyme reaction is the initiation time.

Depending upon the nature of the inhibition of the reagent, additional reagents may be added to prevent inhibition of the endocytosed reagent. The rate of enzyme turnover or the amount of product produced within a fixed time period is related to the activity of the compound in inducing endocytosis. In many instances the occurrence of endocytosis is indicative of the compound activating the surface membrane protein whereby a signal is transduced into the cell.

The method has a number of stages, many of which can use conventional procedures and reagents for their performance: (1) cell preparation; (2) addition of reagent comprising the conjugate of the member of the EFC pair and the member of the binding pair ("bp member"); (3) addition of the test compound; (4) addition of the EFC member inhibitor; (5) lysis of the cells, optionally in the presence of an agent to inactivate the inhibitor; and (6) addition of the reagents for the EFC determination. Each of the steps may involve incubations ranging from about 5 to 120 min, usually about 10 to 90 min. After the cell preparation with the cells in the assay container, usually a tissue culture plate well, the assay is free of any further separations, so that the protocol only requires the addition of liquids and then a reading.

The cell preparation requires that there be a sufficient number of cells for the assay. For the most part, in containers having a capacity in the range of about 100 µl to 1 ml, the number of cells will range from about $1–500\times10^3$ more usually $2–100\times10^3$. The cells may be initially grown in an appropriate serum containing medium under standard tissue culture conditions. However, prior to performing the assay, the media will usually be exchanged with a serum free medium. The cells will be suspended in a volume in relation to the number of cells, generally being in the range of about $10^2–10^5$ cells per microliter.

To the cells in the serum free medium is added the reagent (conjugate of EFC member and bp member) in a small volume, generally equal to or less than the volume of the cell suspension, generally ranging from about 1 to 50 µl, at a concentration in the range of about 25–500 nM, usually about 50–250 nM. The solution of the reagent will generally be a buffered solution, having a buffer concentration in the range of about 10–250 mM. Conventional buffers may be used, such as phosphate buffered saline, Tris-Krebs, Hepes, etc. Other conventional additives may also be included. The assay medium may then be incubated for sufficient time for the reagent to react with the complementary member of the binding pair, generally for a time in the range of about 15 to 120 min at a temperature in the range of about 20 to 40° C., usually about 37° C.

After the prior incubation the test compound or control solution may be added. The same solution used for the reagent may be used for the test compound, although some variation is permitted depending upon the solubility characteristics of the test compound. Depending upon the nature of the test compound, the active range of interest and other considerations relating to the nature of the test compound being assayed, generally volumes of the test compound will be from about 1 to 50 µl. After addition of the test compound or a control solution, the mixture will be incubated for sufficient time for the test compound to bind to the receptor and allow for endocytosis of the receptor. The time may vary from about 15 to 60 min and the temperature will usually be maintained from the prior incubation.

In the next stage, the EFC member bound to the receptor external to the cell will be inactivated. While any mode of inactivation may be used that does not interfere with the remaining steps of the assay, it is found that the use of a protease is particularly advantageous, as it is efficient, rapid and may be readily reversed. Various proteases may be used, individually or in combination, in sufficient amount to ensure that at least substantially all of the EFC member is inactivated. Generally a small volume will be used, usually in the range of about 1–50 µl and the concentration of the protease(s) will depend upon the activity of the protease, the amount of EFC member to be inactivated, and the like. With about 10-2-10-5 nanomoles of EFC member, generally about 0.01 to 5 units/µl will be added, although less or more may be used depending upon the requirements of the assay. The medium will be a buffered medium having a composition that generally optimizes the activity of the protease, such as thrombin, Factor Xa, chymotrypsin, etc. An incubation will usually be employed of short duration, ranging from about 5 to 45 min, which can be conveniently performed at room temperature.

Following the inactivation of the EFC in the external medium, the cells are lysed. Various methods may be employed and the method of lysis is not critical to this invention, although in light of the commercial manner in which the assay will be employed, a lysis reagent is the preferred mode. The lysis reagent must not interfere with the formation of the EFC holoenzyme in the next stage. The reagent may contain specific and/or non-specific protease inhibitors in an amount to sufficiently reduce their activity as to prevent the protease degradation of the remaining internal EFC component. These inhibitors may be exemplified by chymostatin, PMSF, etc. These protease inhibitors should have little or no effect on the EFC holoenzyme.

In addition, a relatively large volume will be employed, generally at least about 0.5–2 times the existing volume of the assay medium prior to the addition of the lysis reagent. Conveniently, a relatively high concentration of an ionic buffer is used in the presence of a relatively high concentration of protein, resulting in osmotic shock and release of the cytosolic contents of the cells. The medium is a conveniently buffered medium that supports the next stage. After incubating for sufficient time for the cells to be lysed, usually in the range of about 5–30 min, generally at an elevated temperature, conveniently in the range indicated previously, the reagents for formation of the EFC holoenzyme and substrate may then be added.

The reagent to form the holoenzyme, i.e. the complementary member of the EFC pair, is added in substantial excess of the range of internalized EFC member that is anticipated. Usually, there will be at least about 1–20× moles of the highest amount of internalized EFC member anticipated. Volumes will be relatively small, generally being the range of about 5–10% of the existing volume of the assay medium. A buffered medium is employed at a pH in the range of about 6.8 to 7.4, usually 6.9 with buffer at a concentration in the range of about 10 to 250 mM. While various conventional buffers may be employed, PIPES has found commercial acceptance. After incubation for sufficient time for the holoenzyme to form, generally being at least about 15 min and not more than about 120 min, the substrate is added, the mixture incubated for sufficient time for a detectable amount of product to be formed, usually requiring at least about 5 min, more usually at least about 10 min and not more than about 60 min.

From the time the test compound is added to the time that the signal is read, the endocytosed EFC member may be subject to degradation or recycling to the surface. It is therefore desirable that the total amount of time for this period does not exceed 240 min, preferably does not exceed 180 min, while still allowing for the desired events to occur, such as endocytosis, degradation of the external EFC member, lysis, formation of the holoenzyme and detection of a signal.

Except in special cases, e.g. lysis, various buffers may be used, such as phosphate, carbonate, borate, MOPS, HEPES, Tris, Krebs, etc., generally at a concentration in the range of about 25 to 250 mM. Other additives may include stabilizers, salts, complexing metal ions, proteins, and the like, generally as conventional additives for the particular stage of the assay.

The first component to be discussed is the surface membrane protein fused to an external member of a specific binding pair. Numerous surface membrane proteins serve as receptors, where when a ligand binds to the receptor, after transducing a signal into the cell, the receptor is endocytosed to form a lysosome, where the receptor is freed of the ligand and may be returned to the surface. There is, therefore, frequently a traffic of the receptor from the surface membrane into the cytosol, so the assay is performed over a period of time that reflects the amount of internalization of the receptor influenced by the candidate compound.

A large number of surface membrane proteins are involved with the transduction of signals and serve as receptors for a wide variety of ligands. For the most part, receptors are defined by the ligand which activates the receptor for transduction or serves to endocytose the ligand. These receptors include endocrine, paracrine and autocrine receptors, G-protein coupled receptors, such as adrenergic receptors, opiate receptors, etc., lipoprotein receptors (including the low-density lipoprotein (LDL) and scavenger receptors), and steroid receptors. These receptors also include surface protein receptors for asialoglycoprotein, insulin, somatostatin, somatotropins, growth factors, such as growth hormone, platelet derived growth factor, insulin-like growth factor, epidermal growth factor (EGF), vascular endothelial growth factor (VEGF). alpha.-transforming growth factor, nerve growth factor, fibroblast growth factor, somatomedin, vasopressin, prostaglandins, eosinophil chemotactic factor, acetylcholine, thyroxine (TSH), epinephrine; endorphins, enkephalins and dynorphins; neurotensin, oxytocin, transferrin, substance P, lymphokines, such as IL-1, -2, -3 and -4, up to -21, etc.; colony stimulating factors. such as GM-CSF, M-CSF, G-CSF, etc.; lipoproteins, such as LDL; and steroids, such as estrogen, androgen, glucocorticoids, corticosteroids, etc. A class of proteins of particular interest and being associated with a large number of different ligands are the G-protein complex receptors (GPCRs). Additional receptors include those receptors employed in the receptor-mediated endocytosis of certain microbial pathogens (e.g. viruses). Receptors of interest are either internalized or are recycled, that is, internalized into the cytoplasm and optionally returned to the plasma membrane surface. Illustrative of the recycled receptors are the receptors for insulin, EGF, LDL, transferrin, interleukins, and asialoglycoprotein.

Fused to the receptor so as to be external to the cell, available to interaction with components of the medium is a member of a specific binding pair. The member of the specific binding pair will be an amino acid sequence of at least about 5, more usually at least about 6 amino acids, particularly at least about 8, more particularly at least about 10 amino acids, and frequently 12 or more amino acids, generally not more than about 30 amino acids, usually not more than about 25 amino acids, and more usually not more than about 20 amino acids. The member may bind to an antibody or antibody fragment, e.g. Fab, a natural binding partner, such as strept/avidin that can bind to a biotin mimetic, a substrate mimetic that can bind to an enzyme, a chelator that can bind to a metal complex, etc. In some instances, where the amino acid member is glycosylated, it may be feasible to use a lectin to bind. The member should not interfere with the binding of a ligand, such as the natural or modified ligand, or an agonist or antagonist, to the receptor, which can be readily determined empirically.

These members have been described in various patents and are conveniently available from Sigma-Aldrich and referred to as FLAG. Since the FLAG epitope has available high affinity antibodies specific for the FLAG epitope, it is very convenient to use the combination in this assay. Using the FLAG epitope and its complementary antibody is primarily a matter of convenience, the reagents are familiar to most investigators in the field, and the epitope is sufficiently rare as not to have a mimetic present on the surface of the cell. FLAG epitopes include Asp-Tyr-Lys-Asp-Asp-Asp-Asp-Lys (SEQ ID NO:1) and Met-Asp-Tyr-Lys-Asp-His-Asp-Gly-Asp-Tyr-Lys-Asp-His-Asp-Ile-Asp-Tyr-Lys-Asp-Asp-Asp-Lys (SEQ ID NO:2). The multiply charged amino acids present provide for a unique conformation and surface charge distribution.

Cells are employed that express the surface membrane protein fused to an external member of a specific binding pair, which will hereinafter be referred to as the "flagged target receptor." To this end, the cells are genetically modified to have an expression construct that expresses the flagged target receptor. The gene will have a signal sequence to direct the flagged target receptor to the surface. For the most part a leader sequence will be employed, although other signals for membrane attachment, such as myristoylation, prenylation, etc. may be employed in some situations, but any attachment to the cell membrane must provide that the bp member is external to the cytosol.

The host cells will be selected to provide the necessary transcription factors for expression of the fusion protein and any other components for the purposes of the determination. The host cells will also be selected toward providing an environment resembling the environment being simulated. In many cases primary cells may be employed, both those maintained in culture and obtained directly from a patient. However, in many other cases, established cell lines will be used, since the cell lines can provide the desired environment and allow for direct comparisons between studies, which comparisons may not be available when using primary cell lines from patients.

Established cell lines, including transformed cell lines, are suitable as hosts. Normal diploid cells, cell strains derived from in vitro culture of primary tissue, as well as primary explants (including relatively undifferentiated cells such as hematopoietic stem cells) are also suitable. Embryonic cells may find use, as well as stem cells, e.g. hematopoietic stem cells, neuronal stem cells, muscle stem cells, etc. Candidate cells need not be genotypically deficient in a selection gene so long as the selection gene is dominantly acting. The host cells preferably will be established mammalian cell lines. For stable integration of vector DNA into chromosomal DNA, and for subsequent amplification of the integrated vector DNA, both by conventional methods, CHO (Chinese Hamster Ovary) cells are convenient. Alternatively, vector DNA may include all or part of the bovine papilloma virus genome (Lusky et al., 1984, Cell 36:391–401) and be carried in cell lines such as C127 mouse cells as a stable episomal element. Other usable mammalian cell lines include HeLa, COS-1 monkey cells, melanoma cell lines such as Bowes cells, mouse L-929 cells, mouse mammary tumor cells, 3T3 lines derived from Swiss, Balb-c or NIH mice, BHK or HAK hamster cell lines and the like.

Cell lines may be modified by knocking out specific genes, introducing specific genes, enhancing or diminishing the expression of a protein or the like. The modification may be transient, as in the case of introduction of antisense DNA, RNAi, or dsRNA or may be permanent, by deleting a gene, introducing a gene encoding the antisense mRNA of the target protein, adding a dominant recessive gene, or the like.

All cells employed will have been genetically modified to have the fusion construct of the label and the receptor. The label may be inserted into the coding region in a variety of ways. The label will be 3' to the signal sequence and 5' to the sequence encoding the receptor, although a few codons may be used for linking, usually not more than about 5, or a few codons may be deleted, usually not more than about 5, where the presence or absence of codons does not significantly affect the purpose of the assay. For a cDNA gene, one may select a suitable restriction site for insertion of the sequence, where by using overhangs at the restriction site, the orientation is provided in the correct direction. Alternatively, one may use constructs that have homologous sequences with the target gene and allow for homologous recombination, where the homologous sequences that are adjacent in the target gene are separated by the label in the construct. By using a plasmid in yeast having the cDNA gene, with or without an appropriate transcriptional and translational regulatory region, one may readily insert the label sequence into the cDNA gene at an appropriate site. Various conventional ways for inserting encoding sequences into a gene can be employed. For expression constructs and decriptions of other conventional manipulative processes, see, e.g., Sambrook, Fritsch & Maniatis, "Molecular Cloning: A Laboratory Manual," Second Edition (1989) Cold Spring Harbor Laboratory Press, Cold Spring Harbor, N.Y. (herein "Sambrook et al., 1989"); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

The gene encoding the fusion protein will be part of an expression construct. The gene is positioned to be under transcriptional and translational regulatory regions functional in the cellular host. The regulatory region may include an enhancer. In many instances, the regulatory regions may be the native regulatory regions of the gene encoding the protein of interest, where the fusion protein may replace the native gene, particularly where the fusion protein is functional as the native protein, may be in addition to the native protein, either integrated in the host cell genome or nonintegrated, e.g. on an extrachromosomal element.

In an initial phase of the development of an assay, one may wish to have a second marker. The second marker may be any marker that allows for detection independently of the label. Such markers include antigenic epitopes that can be recognized by a labeled antibody, antibiotic resistance, polyhistidine that can be detected with a nickel reagent, etc.

In those cells in which the native protein is present and expressed, the fusion protein employing the same expression regulatory region may be competing with the native protein for transcription factors for expression. The site of the gene in an extrachromosomal element or in the chromosome may vary as to transcription level. Therefore, in many instances, the transcriptional initiation region will be selected to be operative in the cellular host, but may be from a virus or other source that will not significantly compete with the native transcriptional regulatory regions or may be associated with a different gene from the gene for the protein of interest, which gene will not interfere significantly with the transcription of the fusion protein.

It should be understood that the site of integration of the expression construct will affect the efficiency of transcription and, therefore, expression of the fusion protein. One may optimize the efficiency of expression by selecting for cells having a high rate of transcription, one can modify the expression construct by having the expression construct joined to a gene that can be amplified and coamplifies the expression construct, e.g. DHFR in the presence of methotrexate, or one may use homologous recombination to ensure that the site of integration provides for efficient transcription. In this way one may overwhelm the expression of the naturally occurring protein, so that the fusion protein is the major determinant of the function of the target protein and its modification in the cell. By inserting an insertion element, such as Cre-Lox at a site of efficient transcription, one can direct the expression construct to the same site. In any event, one will usually compare the enzyme activity from cells in a predetermined environment to cells in the environment being evaluated. One would still retain the naturally occurring protein, which can be analyzed using labeled antibodies to compare the modifications of the naturally occurring protein with the fusion protein.

Depending upon the purpose of the analysis, one may analyze a substantially homogeneous cellular composition or a heterogeneous cellular composition, usually homogeneous. That is, one could have a mixture of cells that are free of the fusion protein and contain the fusion protein. As indicated above, one may wish to analyze the modifications of the naturally occurring target protein for comparison with the fusion protein. Once one has established the relevance of the fusion protein to the characteristics of the naturally occurring protein, the comparison need not be repeated.

There are a large number of commercially available transcriptional regulatory regions that may be used and the particular selection will generally not be crucial to the success of the subject invention. Also, the manner in which the fusion gene construct is introduced into the host cell may vary with the purpose for which the fusion gene is being used. The transcriptional regulatory region may be constitutive or inducible. In the former case, one can have a steady state concentration of the fusion protein in the host, while in the latter case one can provide for going from the substantially total absence (there is the possibility of leakage) to an increasing amount of the fusion protein until a steady state is reached.

Vectors for introduction of the construct include an attenuated or defective DNA virus, such as but not limited to, herpes simplex virus (HSV), papillomavirus, Epstein Barr virus (EBV), adenovirus, adeno-associated virus (AAV), and the like. Defective viruses, appropriately packaged, which entirely or almost entirely lack viral genes, are preferred. Defective virus is not infective after introduction into a cell. Specific viral vectors include: a defective herpes virus 1 (HSV1) vector (Kaplitt et al., 1991, Molec. Cell. Neurosci. 2:320–330); an attenuated adenovirus vector, such as the vector described by Stratford-Perricaudet et al. (1992, J. Clin. Invest. 90:626–630 a defective adeno-associted virus vector (Samulski et al., 1987, J. Virol. 61:3096–3101; Samulski et al., 1989, J. Virol. 63:3822–3828).

The vector may be introduced into the cell by lipofection. For the past decade, there has been increasing use of liposomes for encapsulation and transfection of nucleic acids in vitro. (Feigner, et. al., 1987, Proc. Natl. Acad. Sci. U.S.A. 84:7413–7417; see Mackey, et al., 1988, Proc. Natl. Acad. Sci. U.S.A. 85:8027–8031)). The use of cationic lipids may promote encapsulation of negatively charged nucleic acids, and also promote fusion with negatively charged cell membranes (Felgner and Ringold, 1989, Science 337:387–388).

It is also possible to introduce the vector as a naked DNA plasmid, using calcium phosphate precipitation or other known agent. Alternatively, the vector containing the gene encoding the fusion protein can be introduced via a DNA vector transporter (see, e.g., Wu et al., 1992, J. Biol. Chem. 267:963–967; Wu and Wu, 1988, J. Biol. Chem. 263: 14621–14624; Hartmut et al., Canadian Patent Application No. 2,012,311, filed Mar. 15, 1990).

Vectors are introduced into the desired host cells in vitro by methods known in the art, e.g., transfection, electroporation, microinjection, transduction, cell fusion, DEAE dextran, calcium phosphate precipitation, lipofection (lysosome fusion), use of a gene gun, using a viral vector, with a DNA vector transporter, and the like.

One may use promoters that are active for a short time, such as viral promoters for early genes, for example, the human cytomegalovirus (CMV) immediate early promoter. Other viral promoters include but are not limited to strong promoters, such as cytomegaloviral promoters (CMV), SR.alpha. (Takebe et al., Mole. Cell. Biol. 8:466 (1988)), SV40 promoters, respiratory syncytial viral promoters (RSV), thymine kinase (TK), beta.-globin, etc. Alternatively, an inducible promoter can be used.

A large number of promoters have found use in various situations, for various purposes and for various hosts. Many promoters are commercially available today. Expression of the fusion protein may be controlled by any promoter/enhancer element known in the art, but these regulatory elements must be functional in the host or host cell selected for expression. Promoters which may be used to control fusion gene expression include, but are not limited to, the SV40 early promoter region (Benoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlaufet al., 1985, Mol. Cell. Biol. 5:1639–1648; Hammer et al., 1987, Science 235:53–58), alpha 1-antitrypsin gene control region which is active in the liver (Kelsey et al., 1987, Genes and Devel. 1:161–171), beta-globin gene control region which is active in myeloid cells (Mogram et al., 1985, Nature 315: 338–340; Kollias et al., 1986, Cell 46:89–94), myelin basic protein gene control region which is active in oligodendrocyte cells in the brain (Readhead et al., 1987; Cell 48:703–712), myosin light chain-2 gene control region which is active in skeletal muscle (Sani, 1985, Nature 314:283–286), prostate specific antigen control region, which is active in prostate cells (U.S. Pat. Nos. 6,197,293 and 6,136,792), and gonadotropic releasing hormone gene control region which is active in the hypothalamus (Mason et al., 1986, Science 234:1372–1378). Alternatively, expression of the fusion protein gene can be under control of an inducible promoter, such as metallothionein promoter, which is induced by exposure to heavy metals or a promoter responsive to tetracycline (tet-responsive promoter). For control of the gene transfected into certain brain cells, a glucocorticoid inducible promoter can be used, since glucocorticoids can cross the blood-brain barrier. Alternatively, an estrogen inducible promoter, which would be active in the hypothalamus and other areas responsive to estrogen, can be used. The present invention contemplates the use of any promoter inducible by a pharmacologic agent that can cross the membrane and for neuronal cells, the blood-brain barrier and influence transcription.

Vectors containing DNA encoding the following proteins, for example, have been deposited with the American Type Culture Collection (ATCC) of Rockville, Md.: Factor VIII (pSP64-VIII, ATCC No. 39812); a Factor VIII analog, "LA", lacking 581 amino acids (pDGR-2, ATCC No. 53100); t-PA and analogs thereof (see co-pending U.S. application Ser. No. 882,051); VWF (pMT2-VWF, ATCC No. 67122); EPO (pRK1–4, ATCC No. 39940; pdBPVM-MTneo 342-12 (BPV-type vector) ATCC No. 37224); and GM-CSF (pCSF-1, ATCC No. 39754).

The vector will include the fusion gene under the transcriptional and translational control of a promoter, usually a promoter/enhancer region, optionally a replication initiation region to be replication competent, a marker for selection, as described above, and may include additional features, such as restriction sites, PCR initiation sites, or the like. As described above, there are numerous vectors available providing for numerous different approaches for the expression of the fusion protein in a cellular host.

The next component is the reagent comprising the bp member and the ED. The ED of β-galactosidase is extensively described in the patent literature. U.S. Pat. Nos. 4,378,428; 4,708,929; 5,037,735; 5,106,950; 5,362,625; 5,464,747; 5,604,091; 5,643,734; and PCT application nos. WO96/19732; and WO98/06648 describe assays using complementation of enzyme fragments. The ED will generally be of at least about 35 amino acids, usually at least about 37 amino acids, frequently at least about 40 amino acids, and usually not exceed 100 amino acids, more usually not exceed 75 amino acids. The upper limit is defined by the effect of the size of the ED on the performance and purpose of the determination, the effect on the complementation with the EA, the inconvenience of a larger construct, and the like. The minimum size that can be used must provide a signal that is observable with the products of the cellular events and that can be determined with reasonable sensitivity.

A number of substrates for β-galactosidase are known, where the product is fluorescent. The common substrates are β-D-galactopyranosyl phenols, such as fluorescein, mono- and di-substituted, o-nitrophenyl-β-D-galactoside, β-methylumbelliferyl-β-D-galactoside, X-gal, resorufin-β-D-galactoside, commercially available oxetanes, e.g. Galacto-Light Plus® kits (chemiluminescence) and chlorophenol red. The di-β-D-galactopyranosylfluorescein, and chlorophenol red-β-D-galactopyranoside, or analogous substrates, particularly where the product is inhibited from leaking from the cell, may be used as intracellular markers.

For the most part the binding pair member will be a protein, particularly an antibody. Conveniently, antibodies are commercially available with high affinity for FLAG peptides, so that these can be used and conjugated with the ED. There are numerous ways for conjugating the ED to a protein. Particularly, commercially available EDs normally have a cysteine. By modifying the bp member with maleic anhydride, one can link the ED through a thioether. Alternatively, one could fuse the ED to the protein using genetic methods by employing the gene of the protein fused to a sequence encoding the ED.

The inhibitors for the external ED must not affect the internalized ED. Therefore, methods can be employed that can be differentiated by the cell membrane as a barrier. Any chemical reactant that can be inactivated and that inactivates the ED may be employed. However, for matters of economics and convenience, proteases are preferred, since less of the protease will be required and one need not use large amounts of chemical reagents to first react with the ED and then be inactivated with a different reactant. Proteases that can find use individually or in combination include chymotrypsin, trypsin, bromelain, papain, etc. The amount employed will generally be determined empirically, since one can inactivate the protease and then assay the external ED. In this way, one can readily determine the background resulting from ED that has not been inactivated in the external medium.

The EA reagent is commercially available and has been described in the literature referred to above in relation to the ED.

The reagents may be provided in kits, where the kits could include the cells, either genetically modified or unmodified; if unmodified, the genetic constructs for genetically modifying the cells; the lysis buffer; the EA reagent; the substrate; and standards for comparison of the results.

The following examples are offered by way of illustration and not by way of limitation.

Experimental

Materials

Chinese Hamster Ovary (CHO) cells expressing vasopressin 2 (V2) receptor tagged with FLAG peptide

[Arg8]-Vasopressin (AVP), agonist for V2 receptor (Sigma #V9879)

Anti-FLAG monoclonal antibody (Sigma catalog #F3040) biochemically conjugated to ED4 (The ED was attached to the antibody using N-(γ-maleimidobutyryloxy) sulfosuccinimide ester (Pierce catalog #22324) using standard conjugation procedures. See, U.S. Pat. Nos. 5,120,653 and 5,244,785

Chymotrypsin (Calbiochem #230834)

Cells Lysis Buffer with CHAPS detergent (Roche), BSA fragments (Discoverx), and chymostatin (Calbiochem #230790)

EA Reagent (DiscoveRx)

Chemiluminescense Substrate (Tropix)

Conjugation of Enzyme Donor to AntiFLAG Antibodies

A 3.7 mg/ml solution of the FLAG M1 antibody (Sigma St. Louis, Catalog F3040) in phosphate buffer (1 ml, pH 7.5, 25 mM) was treated with 42 ul of 5 mg/ml freshly prepared solution of sulfoGMBS in water (Pierce, Milwaukee, Wis.; catalog # 22324). The reaction mixture was incubated for 2 hr in an end-over-end shaker. The solution was transferred to a slide-a-lyzer dialysis cassette (10 kDa cutoff, Pierce) and dialyzed in phosphate buffered saline (PBS, Sigma). Two changes at 2 hr intervals followed by an overnight dialysis were performed. A total of 1.1 ml reaction volume was dialyzed against 3×1 L. All of the sample was collected from the dialysis cassette and treated with 133 ul of a 1 mM ED4 (DiscoveRx, Fremont, Calif.) solution. The reaction mixture was incubated for 30 minutes and then transferred to Centricon (Millipore, 30kDa cutoff). Centrifugation at 4000 rpm for 20 minutes using PBS as a wash buffer was repeated until no free ED could be detected in the filtrate. The ED-anti FLAG conjugate was also purified by a Protein A column.

Protocol I

Cell Preparation

Cells are suspended in media with 10% fetal bovine serum, plated in a 96-well tissue culture plate, and allowed to grow overnight under standard tissue culture conditions at 37° C. The next day, media is exchanged and replaced with 50 μL serum free media.

Cell Induction

10 μL of ED labeled anti-FLAG antibody (145 nM reagent concentration) is added to each well, then the plate is incubated for 1 hour at 37° C. (tissue culture incubator). After the incubation is complete, 10 μL agonist or vehicle (assay buffer without agonist) is added to appropriate wells, and the plate is incubated for an additional 30 minutes at 37° C.

Signal Detection

10 μL of Chyrnotrysin Reagent (100 units/mL chymotrypsin, 7 mM EDTA in PBS) is added to all wells, and the plate is incubated for 15 minutes at room temperature. Then 140 μL of Cell Lysis Reagent containing protease inhibitor (0.75% CHAPS, 75 μM chymostatin, 3 mg/mL BSA fragments in a phosphate buffered saline) is added, and incubated for 10 minutes at 37° C. This is followed by the addition of 20 μL of EA Reagent (360 μg/mL EA in a buffered solution with carrier protein) and an incubation of 1 hour at 37° C. In the final step, chemiluminescent substrate (Tropix) is added, incubated at least 20 minutes, and then the signal is read on a luminescence reader.

Figure 1:
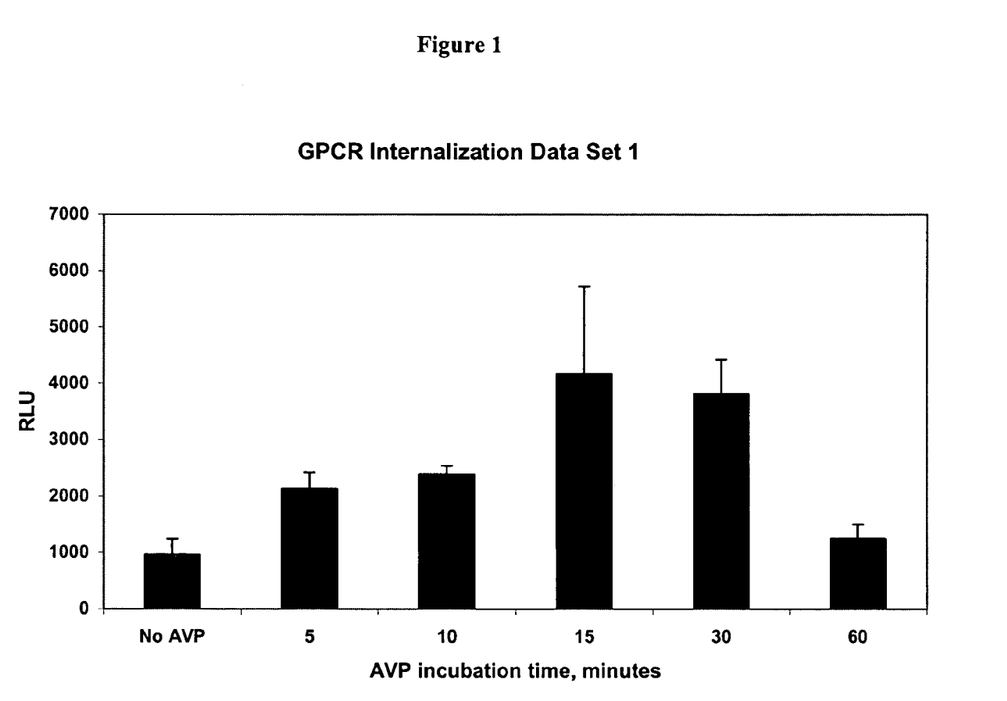
FIG. 1 is a graph showing amount of RLU vs. various incubation times with AVP

An example of Protocol I Results is shown in FIG. 1.

Description of Protocol I Results

CHO cells expressing the V2 receptor tagged with a FLAG sequence were suspended in media containing 10% fetal bovine serum, and plated in a 96-well tissue culture plate at 50,000 cells/well. Cells were allowed to grow overnight in a tissue culture incubator at 37° C. The next day, media was exchanged and replaced with 50 µL serum free media. As a first step in the assay, 10 µL of antibody-ED reagent was added, and then the plate was incubated for 1 hour at 37° C. During this period the antibody-ED conjugate bound to the FLAG-labeled receptors on the surface of the cell. After the incubation period, 10 µL of a V2 agonist, [Arg8]-Vasopressin (AVP) was added to appropriate wells at a system concentration of 1 µM. Vehicle only (cell media) was added to wells containing no AVP. AVP is a known agonist of the V2 receptor, and prolonged exposure to high concentrations causes receptor desensitization and internalization. In this study the AVP was allowed to incubate for 5, 10, 15, 30, or 60 minutes prior to the addition of the Chymotrypsin Reagent (which causes the degradation of un-internalized antibody-ED conjugate). The subsequent signal detection steps were completed as outlined in the protocol. The study results demonstrate that the antibody-ED conjugate binds to the FLAG-tagged receptor, and is increasingly internalized, and protected from chymotrypsin degradation, with increasing exposure to agonist up to thirty minutes. The decreases in signal after thirty minutes of agonist incubation may represent degradation of the conjugate as it is further processed by the endosomes.

It is evident from the above results that a convenient assay is provided for determining endocytosis of cell membrane receptors. The protocol allows for all of the steps after growth of the cells to be performed by continuous additions of reagents, rather than removal of media and providing other media. The assay is shown to be sensitive and can be performed in time periods that allow for accurate determination of the amount of endocytosis, despite intracellular events that may involve degradation of the EFC member. By having an assay protocol without separation and washing steps, one avoids the inherent errors introduced by separation and washing steps and greatly simplifies the use of automation to perform the assay. The use of a single vessel for each determination adds great flexibility to the use of the subject protocol. The consecutive addition of reagents is found not to diminish the efficiency of the determination, in that the reagents are found not to be interfering. Rather, one can carry out the assay in the presence of the various reagents that have been added during the protocol.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for determining endocytic changes of a cell membrane receptor in cells as a result of a change of environment of said cells, where said cells have a labeled cell membrane receptor, said label being (1) bound to said cell membrane receptor, (2) a first member of a specific binding pair and (3) external to said cell membrane, and said method including as a reagent a complementary member of said specific binding pair joined to a member of an enzyme fragment complementation pair, which when complexed to a complementary enzyme fragment forms an active enzyme, said method comprising:
  adding said reagent to said cells, wherein said reagent becomes bound to said labeled cell membrane receptor;
  producing an environment to be tested for its effect on endocytosis for said cells to which said reagent is bound;
  inactivating any of said member of said enzyme fragment complementation pair with an inactivating agent that does not adversely affect the activity of any member of said enzyme fragment complementation pair that has undergone endocytosis;
  deactivating said inactivating agent;
  lysing said cells;
  adding said complementary enzyme fragment and a substrate; and
  determining the amount of product produced from said substrate;
  wherein the amount of product is related to the amount of endocytosis of said cell membrane receptor.

2. A method according to claim 1, wherein said inactivating agent is a protease and said deactivating employs a protease inhibitor.

3. A method according to claim 1, wherein said label is a FLAG label and said complementary member of said binding pair is an anti-FLAG antibody.

4. A method according to claim 1, wherein said producing the environment is the inclusion of a test compound.

5. A method according to claim 1, wherein said cells are a mammalian cell line genetically modified to express said labeled cell membrane receptor constitutively.

6. A method for determining endocytic changes of a cell membrane receptor in mammalian cells as a result of a change of environment of said cells where said cells are suspended in a medium and genetically modified to express a labeled cell membrane receptor, said label being a polypeptide and a first member of a specific binding pair, and external to said cell membrane, and said method including as a reagent a complementary antibody to said polypeptide joined to a β-galactosidase member of an enzyme fragment complementation pair which, when complexed to the complementary enzyme fragment, forms an active β-galactosidase, said method comprising:
  adding said reagent to said cells suspended in a medium and incubating for sufficient time for said reagent to bind to said label of said cell membrane receptor;
  adding a test compound to said cells to determine the effect of said test compound on endocytosis of said cell membrane receptor wherein other than endocytosed reagent remains bound to said labeled cell membrane receptor and said β-galactosidase member of said reagent remains external to said cell membrane;
  degrading external β-galactosidase member of said enzyme fragment complementation pair with at least one protease;
  deactivating said at least one protease;
  lysing said cells by osmotic shock;
  adding said complementary enzyme fragment and a substrate; and
  determining the amount of product produced from said substrate;
  wherein the amount of product is related to the amount of endocytosis of said cell membrane receptor.

7. A method according to claim 6, wherein said polypeptide is a FLAG polypeptide.

8. A method according to claim 6, wherein said product gives a chemiluminescent signal.

9. A method according to claim 6, wherein said at least one protease includes chymotrypsin.

10. A kit comprising:
  (1) (a) a mammalian cell comprising an expression construct expressing a cell membrane receptor fused at its external end to a polypeptide label or (b) an expression construct expressing a cell membrane receptor fused at its external end to a polypeptide label;
  (2) antibody to said polypeptide label joined to a first β-galactosidase fragment; and
  (3) a complementary second β-galactosidase fragment that when complexed with said first fragment forms an active enzyme.

* * * * *

UNITED STATES PATENT AND TRADEMARK OFFICE
CERTIFICATE OF CORRECTION

PATENT NO. : 7,202,043 B2  
APPLICATION NO. : 11/244256  
DATED : April 10, 2007  
INVENTOR(S) : Yun-Jung Choi et al.

Page 1 of 1

It is certified that error appears in the above-identified patent and that said Letters Patent is hereby corrected as shown below:

Title page, item (73) Assignee: DiscoveRx Corporation, Fremont, CA US

Signed and Sealed this

Third Day of July, 2007

JON W. DUDAS  
*Director of the United States Patent and Trademark Office*